(12) United States Patent
Sramek

(10) Patent No.: US 10,758,415 B2
(45) Date of Patent: Sep. 1, 2020

(54) METHOD AND APPARATUS FOR USING MULTI-CLAD FIBER FOR SPOT SIZE SELECTION

(71) Applicant: Topcon Medical Systems, Inc., Oakland, NJ (US)

(72) Inventor: Chris Sramek, Half Moon Bay, CA (US)

(73) Assignee: Topcon Medical Systems, Inc., Oakland, NJ (US)

( * ) Notice: Subject to any disclaimer, the term of this patent is extended or adjusted under 35 U.S.C. 154(b) by 28 days.

(21) Appl. No.: 15/873,129

(22) Filed: Jan. 17, 2018

(65) Prior Publication Data
US 2019/0216642 A1 Jul. 18, 2019

(51) Int. Cl.
| | | |
|---|---|---|
| *A61F 9/008* | (2006.01) | |
| *G02B 6/32* | (2006.01) | |
| *G02B 6/036* | (2006.01) | |
| *A61B 3/14* | (2006.01) | |
| *A61B 3/00* | (2006.01) | |
| *A61B 90/00* | (2016.01) | |
| *A61B 18/20* | (2006.01) | |

(52) U.S. Cl.
CPC ............ *A61F 9/008* (2013.01); *A61B 3/0008* (2013.01); *A61B 3/14* (2013.01); *A61F 9/00823* (2013.01); *G02B 6/036* (2013.01); *G02B 6/32* (2013.01); *A61B 2018/205547* (2017.05); *A61B 2090/3614* (2016.02); *A61F 2009/00863* (2013.01)

(58) Field of Classification Search
CPC .................................. G02B 6/36; A61F 9/008
USPC .......................................................... 385/33
See application file for complete search history.

(56) References Cited

U.S. PATENT DOCUMENTS

| | | | | | |
|---|---|---|---|---|---|
| 3,711,262 A | * | 1/1973 | Keck | ...................... | C03B 19/01 |
| | | | | | 65/417 |
| 4,076,378 A | * | 2/1978 | Cole | .................... | G02B 6/4298 |
| | | | | | 385/115 |
| 4,230,472 A | * | 10/1980 | Schultz | ................. | C03B 37/014 |
| | | | | | 65/416 |
| 4,363,533 A | * | 12/1982 | Stowe | ................... | G02F 1/0134 |
| | | | | | 367/141 |
| 4,830,453 A | * | 5/1989 | Khoe | ................... | G02B 6/4204 |
| | | | | | 385/35 |

(Continued)

FOREIGN PATENT DOCUMENTS

| | | |
|---|---|---|
| WO | 2006014392 A1 | 2/2006 |
| WO | 2017049085 A1 | 3/2017 |

OTHER PUBLICATIONS

Invitation to Pay Additional Fees dated Apr. 25, 2019, in connection with International Patent Application No. PCT/US2019/012274, 11 pgs.

(Continued)

*Primary Examiner* — Kaveh C Kianni
(74) *Attorney, Agent, or Firm* — Chiesa Shahinian & Giantomasi PC

(57) ABSTRACT

A method and system for spot size selection wherein an indication of a spot size selection is received and a spot size is generated corresponding to the spot size selection by propagating an optical signal via one of the claddings of a dual-clad optical fiber. The system for spot size selection includes a plurality of lens arrays, at least one galvanometer, and a plurality of dual-clad fibers to propagate an optical signal from one of the plurality of lens arrays.

9 Claims, 3 Drawing Sheets

(56) References Cited

U.S. PATENT DOCUMENTS

| | | | | |
|---|---|---|---|---|
| 5,207,669 | A * | 5/1993 | Baker | A61B 18/245 606/15 |
| 5,420,948 | A * | 5/1995 | Byron | G02B 6/021 359/573 |
| 5,557,699 | A * | 9/1996 | Kester | G02F 3/00 359/328 |
| 5,633,965 | A * | 5/1997 | Bricheno | G02B 6/29334 385/37 |
| 5,721,800 | A * | 2/1998 | Kato | G02B 6/02009 385/127 |
| 5,913,005 | A * | 6/1999 | Terasawa | G02B 6/02009 385/124 |
| 5,946,439 | A * | 8/1999 | Terasawa | G02B 6/02009 385/123 |
| 6,477,295 | B1 * | 11/2002 | Lang | G02B 6/2817 372/6 |
| 7,274,012 | B2 * | 9/2007 | Itoh | B82Y 20/00 250/227.11 |
| 7,414,729 | B2 | 8/2008 | Xie et al. | |
| 7,447,408 | B2 | 11/2008 | Bouma et al. | |
| 7,599,591 | B2 | 10/2009 | Andersen et al. | |
| 7,768,700 | B1 * | 8/2010 | Savage-Leuchs | B29C 48/255 359/341.1 |
| 7,835,608 | B2 * | 11/2010 | Minelly | G02B 6/03638 385/126 |
| 7,889,348 | B2 | 2/2011 | Tearney et al. | |
| 8,000,576 | B2 | 8/2011 | Chen et al. | |
| 9,270,080 | B1 * | 2/2016 | Clowes | H01S 3/094003 |
| 9,407,059 | B2 * | 8/2016 | Pomeranz | H01S 5/0092 |
| 2002/0054738 | A1 * | 5/2002 | Matsushima | G02B 6/10 385/50 |
| 2002/0181910 | A1 * | 12/2002 | Holmes | G02B 6/0281 385/124 |
| 2004/0114859 | A1 * | 6/2004 | Colgan | G02B 6/3636 385/31 |
| 2004/0151467 | A1 * | 8/2004 | Ishikawa | G02B 6/02085 385/144 |
| 2005/0163424 | A1 * | 7/2005 | Chen | G01F 1/6884 385/37 |
| 2005/0175059 | A1 * | 8/2005 | Leclair | G02B 6/03622 372/102 |
| 2005/0281508 | A1 * | 12/2005 | Krupkin | H01S 3/094003 385/36 |
| 2006/0013544 | A1 | 1/2006 | Bouma et al. | |
| 2007/0126985 | A1 | 6/2007 | Wiltberger et al. | |
| 2007/0237453 | A1 * | 10/2007 | Nielsen | G02B 6/02004 385/28 |
| 2007/0274650 | A1 * | 11/2007 | Tearney | A61B 1/00082 385/118 |
| 2008/0193093 | A1 * | 8/2008 | DiGiovanni | G02B 6/0365 385/115 |
| 2008/0247424 | A1 * | 10/2008 | Sacks | H01S 3/06716 372/6 |
| 2008/0267228 | A1 * | 10/2008 | Sacks | G02B 6/14 372/6 |
| 2009/0024191 | A1 * | 1/2009 | Seibel | A61B 1/0008 607/92 |
| 2009/0080469 | A1 * | 3/2009 | Nikolajsen | G02B 6/2817 372/6 |
| 2009/0129721 | A1 * | 5/2009 | Chen | G01F 23/292 385/12 |
| 2009/0135877 | A1 * | 5/2009 | Yang | H01S 5/10 372/50.11 |
| 2009/0310904 | A1 * | 12/2009 | Matsubara | G02B 6/12002 385/14 |
| 2010/0044106 | A1 * | 2/2010 | Zediker | E21B 7/14 175/16 |
| 2010/0141466 | A1 * | 6/2010 | Nguyen | H04L 49/30 340/687 |
| 2010/0228119 | A1 * | 9/2010 | Brennan | A61B 3/10 600/424 |
| 2010/0296157 | A1 * | 11/2010 | Takahashi | H01S 3/094003 359/341.3 |
| 2011/0141861 | A1 * | 6/2011 | Hirata | G11B 5/02 369/13.33 |
| 2011/0205349 | A1 * | 8/2011 | Li | G02B 6/02342 348/65 |
| 2011/0275899 | A1 | 11/2011 | Tearney et al. | |
| 2012/0069721 | A1 * | 3/2012 | Nishida | B82Y 10/00 369/13.33 |
| 2012/0127459 | A1 | 5/2012 | Handerek | |
| 2012/0154783 | A1 | 6/2012 | Goldberg et al. | |
| 2012/0165905 | A1 | 6/2012 | Liesfeld et al. | |
| 2012/0165906 | A1 | 6/2012 | Liesfeld et al. | |
| 2012/0275015 | A1 * | 11/2012 | Takanashi | H01S 3/094007 359/341.3 |
| 2012/0302862 | A1 | 11/2012 | Yun et al. | |
| 2013/0016743 | A1 * | 1/2013 | Tanaka | G02B 6/02366 372/6 |
| 2013/0087694 | A1 * | 4/2013 | Creeden | G01J 1/0425 250/227.11 |
| 2015/0055916 | A1 * | 2/2015 | Tanaka | G02B 6/2856 385/43 |
| 2015/0086153 | A1 * | 3/2015 | Ono | G02B 6/34 385/11 |
| 2016/0178439 | A1 * | 6/2016 | Freudiger | G01J 3/44 356/301 |
| 2016/0336710 | A1 * | 11/2016 | Tanaka | H01S 3/06729 |
| 2017/0299900 | A1 * | 10/2017 | Montoya | G02F 1/0115 |
| 2019/0053745 | A1 * | 2/2019 | Nakaji | A61B 5/053 |
| 2019/0175300 | A1 * | 6/2019 | Horn | A61B 90/30 |
| 2019/0175407 | A1 * | 6/2019 | Bacher | A61B 18/22 |
| 2019/0212761 | A1 * | 7/2019 | Swanson | A61B 1/07 |
| 2019/0229489 | A1 * | 7/2019 | Matsumoto | G02B 6/02 |
| 2019/0237929 | A1 * | 8/2019 | Matsumoto | H01S 3/06716 |
| 2019/0319422 | A1 * | 10/2019 | Kitahara | H01S 3/067 |

OTHER PUBLICATIONS

International Search Report and Written Opinion dated Jun. 21, 2019 in connection with International Patent Application No. PCT/US2019/012274, 15 pgs.

Yelin et al., "Double-clad fiber for endoscopy," Optics Letters, vol. 29, No. 20, Oct. 15, 2004, pp. 2408-2410.

* cited by examiner

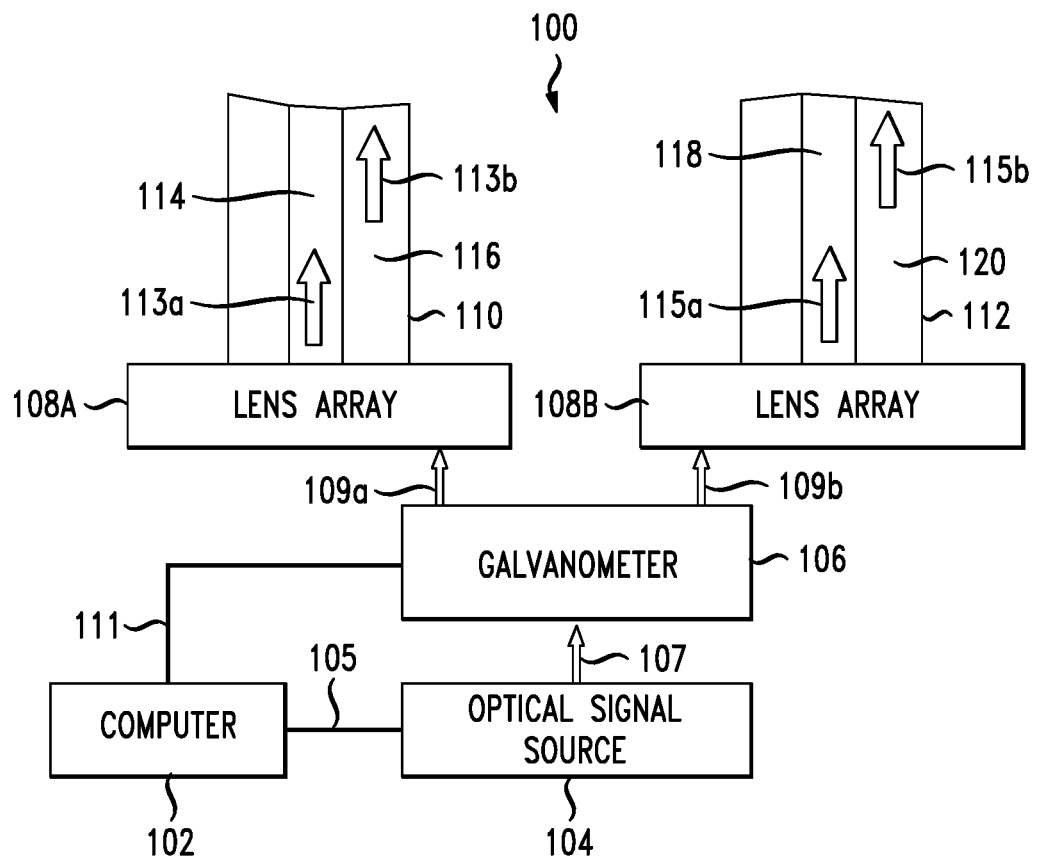
FIG. 1
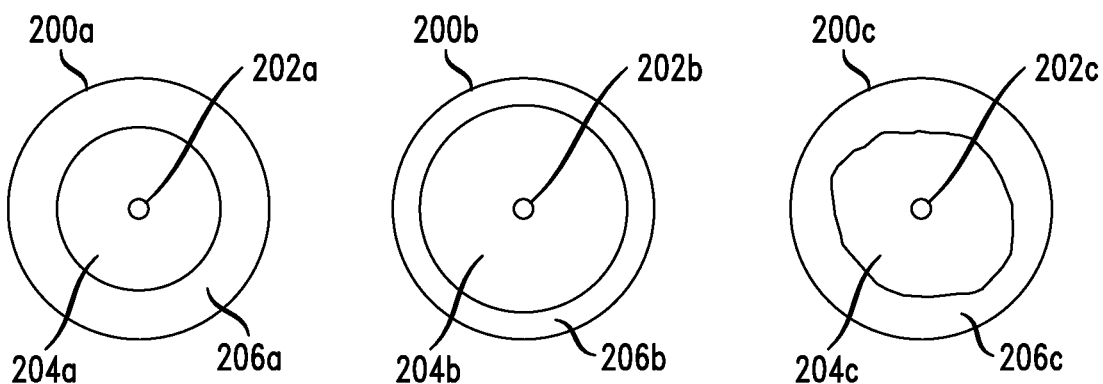
FIG. 2A
PRIOR ART
FIG. 2B
PRIOR ART
FIG. 2C
PRIOR ART

METHOD AND APPARATUS FOR USING MULTI-CLAD FIBER FOR SPOT SIZE SELECTION

TECHNICAL FIELD

The present invention relates generally to optical imaging, and more particularly to a method and system for using multi-clad fiber for selecting an optical signal in a form of an optical beam having a particular radius where the optical beam is to be used in a variety of procedures such as ophthalmic procedures (i.e., spot size selection in ophthalmic procedures) and photomedicine applications.

BACKGROUND

As is known in the art, fiber optic endoscopy is typically conducted by transmitting an image through an array of fibers often referred to as a fiber bundle. While successful for a variety of medical and non-medical applications, utilization of an array of fibers to form the image imposes constraints on the cost, diameter, and flexibility of the imaging device. In an attempt to overcome these drawbacks, multiple approaches employing a single optical fiber have been proposed for miniature, flexible endoscopes. For example, one technique for confocal imaging with a single fiber has been implemented by utilizing the core of a single-mode fiber as both the source and the detection apertures. Also, miniature confocal microscope probes and endoscopes have been constructed by adding a mechanical micro-scanner at the tip of a single-mode fiber. Another single-fiber method for miniature endoscopy (referred to as spectral encoding) uses a broadband light source and a diffraction grating to spectrally encode reflectance across a transverse line within the sample.

In ophthalmic treatments it is common to use an optical beam to treat a patient's eye, for example, using visible laser light to treat diabetic retinopathy and age-related macular degeneration. Traditionally, adjustable optical beam diameters have been produced using a fixed light source with either a zoom lens or turret assembly to vary the magnification level. Alternatively, the optical beam may be defocused by changing the distance between the target and the last lens in the chain of optical elements to vary the beam spot size. While these techniques vary the beam spot size satisfactorily, they involve moving elements with large moments of inertia that lead to increases in fabrication costs and have speed limitations on beam spot adjustment.

To address certain of these shortcomings, other systems have been developed that have the ability to adjust beams, spot sizes and spot shapes, for example at the treatment plane to overcome some of the above-identified limitations. For example, U.S. Pat. No. 7,599,591 issued to D. E. Andersen et al. describes an optical delivery system and method for providing adjustable beam diameter, spot size and/or spot shape by modifying optical characteristics of beams, varying objects such as fibers or other optical elements, etc., to achieve final beam diameter of a desired size and shape.

As disclosed in other prior described systems, the core of the single-mode fiber acts as both the source and the detection apertures for these techniques. As is also known, one important design parameter for single-fiber endoscopy is the modal profile of the optical fiber. Single-mode optical fibers enable high resolution imaging with small and flexible imaging probes, but suffer from relatively poor light throughput. Furthermore, the small core of the single-mode fiber acts similarly to a pinhole in free-space confocal microscopy, preventing the detection of out-of-focus light. For endoscopic applications, this optical sectioning may not be desirable since a large depth of field, large working distance, and wide field of view are typically preferred. For endoscopic microscopy applications, optical sectioning may be sacrificed for increased light throughput. When illuminated by coherent sources, imaging via single-mode fibers also introduces so-called speckle noise, which significantly reduces the effective resolution and quality of the images.

Replacing the single-mode fiber with a relatively large diameter multi-mode optical fiber enables higher optical throughput and decreases speckle noise. Unfortunately, utilization of a large diameter multi-mode fiber severely deteriorates the system's point-spread function and prevents the use of interferometry for high sensitivity and three-dimensional detection. Recently, significant progress has been made developing high power fiber lasers utilizing double-clad (also called "dual-clad") optical fibers. These fibers are unique in their ability to support single mode propagation through the core with multi-mode propagation through the inner cladding.

Therefore, a need exists for an improved technique of spot size adjustment utilizing multi-clad fibers.

BRIEF SUMMARY OF THE EMBODIMENTS

The various embodiments herein generally relate to optical imaging, and more particularly to a method and system for using multi-clad fiber in ophthalmic procedures for spot size selection, i.e., selection of an optical signal presented in the form of an optical beam having a particular radius. In an embodiment, an optical system is provided which includes a plurality of lens arrays, one or more galvanometers, and a plurality of double-clad fibers (also referred to herein as "dual-clad fiber(s)") to propagate an optical signal. Each of the plurality of dual-clad fibers includes a core and two claddings where one (i.e., inner) cladding surrounds the core and where the other (i.e., outer) cladding surrounds the inner cladding of the dual-clad fiber.

In an embodiment, a method is provided for spot size selection in ophthalmic procedures in which an indication of a spot size selection is received from a user and a spot size corresponding to the spot size selection is generated by propagating an optical signal through an optical system via one of the claddings of a dual-clad optical fiber.

Advantageously, the various embodiments herein provide an improved technique for varying an optical characteristic of an optical beam, i.e., spot size adjustment, through the use of a multi-clad fiber and selectively targeting the core or cladding(s) of such fiber. This facilitates selectively directing and/or redirecting the optical signal to the core or cladding(s)) to deliver the desired adjusted spot size.

These and other advantages of the embodiments will be apparent to those of ordinary skill in the art by reference to the following detailed description and the accompanying drawings.

BRIEF DESCRIPTION OF THE DRAWINGS

FIG. 1 illustrates an apparatus having a multi-clad fiber for spot size selection in ophthalmic procedures in accordance with an embodiment;

FIGS. 2A, 2B, and 2C illustrate exemplary dual-clad optical fibers as described in the prior art;

DETAILED DESCRIPTION

Figure 3:
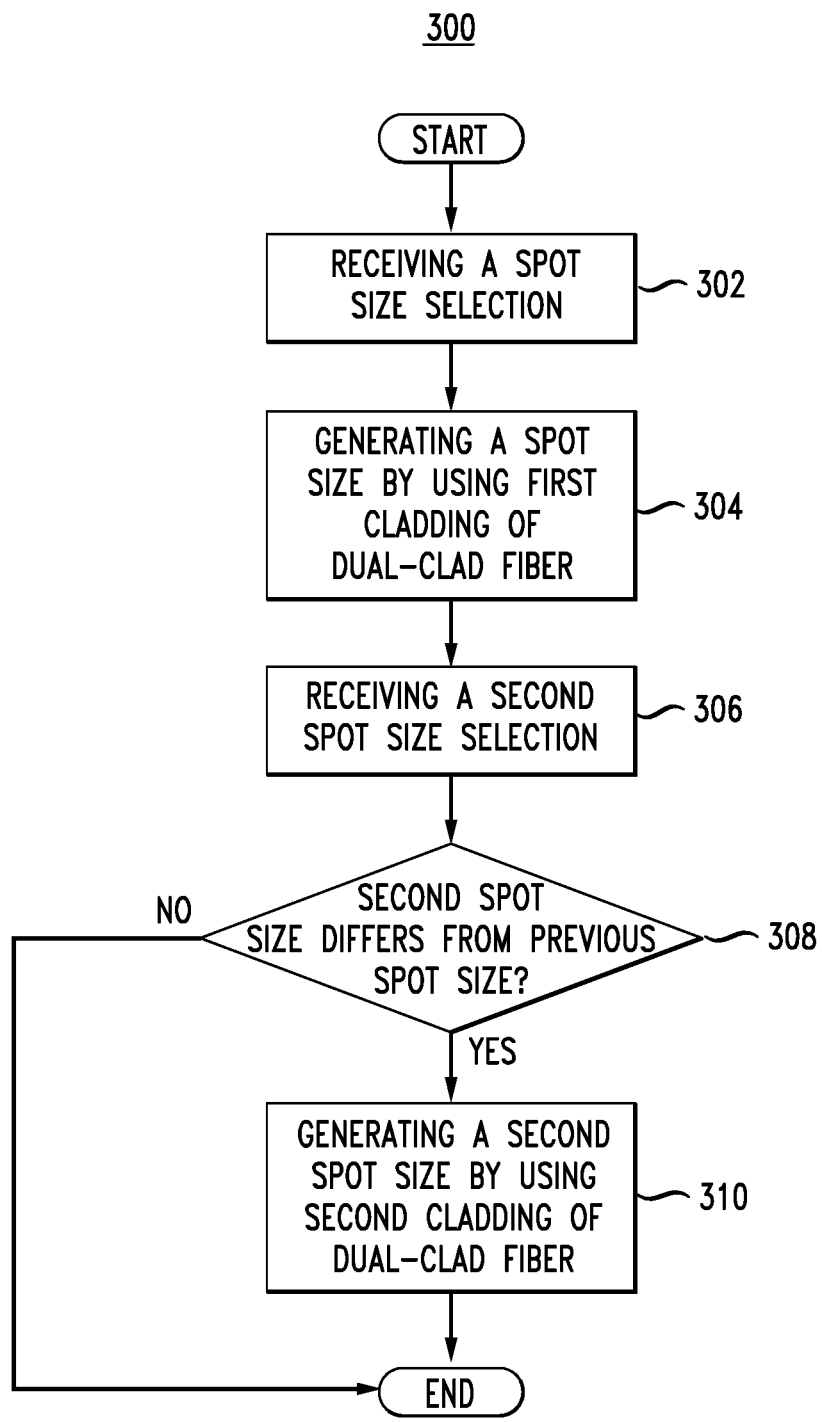
FIG. 3 shows a flowchart of illustrative operations for spot size selection in ophthalmic procedures according to an embodiment.

The various embodiments herein generally relate to optical imaging, and more particularly, to a method and system for using multi-clad fiber in ophthalmic procedures for spot size selection, i.e., selection of an optical signal presented in the form of an optical beam having a particular radius. In an embodiment, an optical system is provided which includes a plurality of lens arrays, one or more galvanometers, and a plurality of dual-clad fibers to propagate an optical signal. Each of the plurality of dual-clad fibers includes a core and two claddings where one (i.e., inner) cladding surrounds the core and where the other (i.e., outer) cladding surrounds the inner cladding of the dual-clad fiber. As will be appreciated, the principles encompassed in the ophthalmic embodiments detailed herein apply equally to other applications such as photomedicine or other applications requiring the delivery of precise spot size selection and/or adjustment.

FIG. 1 illustrates optical system 100 having a multi-clad fiber for spot size selection in ophthalmic procedures according to an embodiment. Optical system 100 includes a plurality of dual-clad fibers 110 and 112 where each of the dual-clad fibers 110 and 112 is capable of generating more than one spot size as described in detail herein below. Optical system 100 also includes computer 102, optical signal source 104, at least one galvanometer 106 and a plurality of lens arrays 108A and 108B. In the embodiment, dual-clad fibers 110 and 112 are identical or substantially identical (i.e., having an identical or substantially identical configuration and dimensions of a core and claddings). In a further embodiment, dual-clad fibers 110 and 112 differ more significantly (i.e., dual-clad fiber 110 having a configuration and dimensions of a core and claddings that are different from a configuration and dimensions of a core and claddings of dual-clad fiber 112).

FIGS. 2A, 2B, and 2C illustrate exemplary known dual-clad optical fibers 200a, 200b, and 200c, respectively. It is to be understood that any of the dual-clad fibers 200a, 200b, or 200c may be used in optical system 100 as dual-clad fibers 110 and 112. As shown in FIGS. 2A-2C, while each dual-clad fiber 200a, 200b, and 200c includes a centrally-placed core 202a, 202b, and 202c, respectively, the diameter of claddings 204a and 206a can differ from diameters 204b and 206b. It is to be understood that cladding shape can be different from a traditional radial configuration. For example, FIG. 2C illustrates dual-clad fiber 200c which has one such cladding shape for cladding 204c and 206c. It is also to be understood that while dual-clad optical fiber 200a may be used as dual-clad fiber 110 and dual-clad optical fiber 200b may be used as dual-clad fiber 112. It is also to be understood that optical system 100 may employ any combination of known dual-clad fibers.

Returning to FIG. 1, in accordance with an embodiment, optical signal source 104, controlled by computer 102, via communication channel 105, emits optical signal 107 which is propagated to galvanometer 106. In one embodiment, galvanometer 106 is controlled by computer 102, via communication channel 111, to change orientation of its reflective surfaces in three-dimensional space. Change of orientation of reflective surfaces of galvanometer 106 allows re-direction of optical signal 107 to be directed to lens arrays 108A and/or 108B. For example, galvanometer 106 may be oriented in such a way that optical signal 107 is directed, as optical signal 109a, to lens array 108A. In another example, galvanometer 106 may be oriented in such a way that optical signal 107 is directed, as optical signal 109b, to lens array 108B. In yet another example, galvanometer 106 may be oriented in such a way that optical signal is split to be directed to lens array 108A and to lens array 108B simultaneously. It is to be understood that although FIG. 1 shows only two lens arrays 108A and 108B, optical system 100 may have any number of lens arrays and associated configurations.

As shown in FIG. 1, each of lens arrays 108A and 108B is associated with a dual-clad fiber. Specifically, lens array 108A is associated with dual-clad fiber 110 and lens array 108B is associated with dual-clad fiber 112. It is to be understood that although FIG. 1 shows each of lens arrays 108A and 108B being associated with one dual-clad fiber, each lens array may be associated with any number of dual-clad fibers.

Each of lens arrays 108A and 108B includes one or more optical lenses situated in such a way as to modify the geometry of an optical signal it propagates. Optical lenses included in each of the plurality of lens arrays may be converging lenses, diverging lenses, collimating lenses, or any combination thereof.

Upon modifying the geometry of optical signal, the lens arrays output the modified optical signal, via the dual-clad fiber, to a user of the optical system 100. Specifically, lens array 108A is configured to modify the geometry of optical signal 109a and transmit modified optical signal to a user of optical system 100 by redirecting optical signal 109a to inner clad 114 of dual-clad fiber 110 (i.e., optical signal 113a) or outer clad 116 of dual-clad fiber 110 (i.e., optical signal 113b), depending on the requested spot size selection by the user. Similarly, lens array 108B is configured to modify the geometry of optical signal 109b and transmit modified optical signal to a user of optical system 100 by redirecting optical signal 109b to inner clad 118 of dual-clad fiber 112 (i.e., optical signal 115a) or outer clad 120 of dual-clad fiber 112 (i.e., optical signal 115b), depending on the requested spot size selection by the user. It is to be understood that lens arrays 108A can redirect optical signal 109a to inner clad 114 of dual-clad fiber 110 or outer clad 116 of dual-clad fiber 110 simultaneously. Similarly, lens array 108B can redirect optical signal 109b to inner clad 118 of dual-clad fiber 112 and outer clad 120 of dual-clad fiber 112 simultaneously.

Advantageously, the various embodiments herein provide an improved technique for varying an optical characteristic of an optical beam, i.e., spot size adjustment, through the use of a multi-clad fiber and selectively targeting the core or cladding(s) of such fiber (i.e., selectively directing and/or redirecting the optical signal to the core or cladding(s)) to deliver the desired adjusted spot size.

It is to be understood that optical system 100 employs dual-clad fibers 108A and 108B individually depending on a functional architecture of optical system 100 and depending on the need of a user of the optical system 100 to select an optical signal having a particular spot-size appropriate for a certain procedure.

For example, if a user of optical system 100 requires an optical signal to have a first spot-size (e.g., 50 μm) for an ophthalmic procedure, computer 102 controls optical signal source 104 to generate optical signal 107, propagates optical signal 107 to galvanometer 106 which causes redirection of optical signal (i.e., optical signal 109a) to lens array 108A. In turn, lens array 108A modifies the geometry of optical signal 109a to generate optical signal 113a to be propagated via inner clad 114 of dual-clad fiber 110 to transmit an image to a user of the optical system 100.

If a user of optical system 100 requires an optical signal to have a second spot-size (e.g., where the second spot-size is different from the first spot-size, illustratively, 100 µm) for an ophthalmic procedure, computer 102 controls optical signal source 104 to generate optical signal 107, propagate optical signal 107 to galvanometer 106 which causes redirection of optical signal (i.e., optical signal 109a) to lens array 108A. In turn, lens array 108A modifies the geometry of optical signal 109a to generate optical signal 113b to be propagated via outer clad 116 of dual-clad fiber 110 to transmit an image to a user of the optical system 100.

If a user of optical system 200 requires an optical signal to have a third spot-size (e.g., where the third spot-size is different from the second spot-size and the first spot-size, illustratively, 200 µm) for an ophthalmic procedure, computer 102 controls optical signal source 104 to generate optical signal 107, propagate optical signal 107 to galvanometer 106 which causes redirection of optical signal (i.e., optical signal 109b) to lens array 108B. In turn, lens array 108B modifies the geometry of optical signal 109b to generate optical signal 115a to be propagated via inner clad 118 of dual-clad fiber 112 to transmit an image to a user of the optical system 100.

If a user of optical system 100 requires an optical signal to have a fourth spot-size (e.g., where the fourth spot-size is different from the third spot-size, the second spot-size, and the first spot-size, illustratively, 400 µm) for an ophthalmic procedure, computer 102 controls optical signal source 104 to generate optical signal 107, propagate optical signal 107 to galvanometer 106 which causes redirection of optical signal (i.e., optical signal 109b) to lens array 108B. In turn, lens array 108B modifies the geometry of optical signal 109b to generate optical signal 115b to be propagated via outer clad 120 of dual-clad fiber 112 to transmit an image to a user of the optical system 100.

FIG. 3 shows a flowchart of illustrative operations 300 for spot size selection in ophthalmic procedures according to an embodiment. Illustratively, operations 300 are utilized by optical system 100 (see, FIG. 1) in generating a requested spot-size for ophthalmic procedures. In accordance with the embodiment, optical system 100 will initiate the method, at step 302, for receiving a spot size selection (illustratively, as indicated from the user of optical system 100). The indication of a spot size selection can be in a form of an electronic signal sent by an input device used by a user of the optical system (e.g., ophthalmic equipment) to enter a command to select an appropriate spot size. The input device used by a user can be a user interface that allows a user to enter commands in a variety of well-known ways such as by pressing one or more buttons, pressing one or more areas on touch-screen of the user interface, engaging a manual controller (e.g., joystick), providing a voice command, or using a haptic device.

At step 304, generating the requested spot size using the first cladding of the dual-clad fiber is undertaken in response to receiving the spot size selection. In the embodiment, upon receiving the spot size selection, the optical signal generated by optical signal source 104 of optical system 100 is propagated to galvanometer 106 which causes redirection of optical signal to a lens array. In turn, a lens array modifies the geometry of optical signal and propagates a geometrically-modified optical signal to a user of optical system 100 via one of the claddings of a dual-clad fiber. A person skilled in the art will understand that optical system 100 may contain any number of dual-clad fibers to accommodate propagation of optical signal having a desired spot-size.

At step 306, the method continues by receiving a second spot size selection (again, illustratively, from a user of optical system 100). The indication of the second spot size selection can be in a form similar to the one as discussed at step 302 above. Provided that the second spot size selection differs from the previous spot size selection (see, step 308, where such a determination is performed), step 310 continues in generating the indicated second spot size using the second cladding of the dual-clad fiber, as detailed herein above, in response to receiving the second spot size selection. In the embodiment, the second spot size is generated by switching the propagation of the optical signal from a one cladding of the dual-clad fiber to one other cladding of the dual-clad fiber. A person skilled in the art will understand that characteristics of the two claddings of the dual-clad fiber must differ, such as the depth of each cladding, its positioning (i.e., inner or outer) respective to a core of the dual-clad fiber, configuration of boundaries of each cladding, and the like. It is to be understood that, while the exemplary embodiment of the present disclosure illustrates a dual-clad fiber for spot size selection in ophthalmic procedures, the optical system can use an optical fiber containing any number of cladding(s) for spot size selection.

As detailed above in the illustrative embodiments, galvanometers are utilized in selectively propagating the optical signal by targeting the core or one of the claddings of the multi-clad fiber. Of course, it will be understood that this is illustrative in nature and the selective targeting of the core and/or claddings can be accomplished in embodiments by any means such as adjusting the relative position of the optical fiber and beam, or by adjusting the spot size or divergence, to name just a few.

Figure 4:
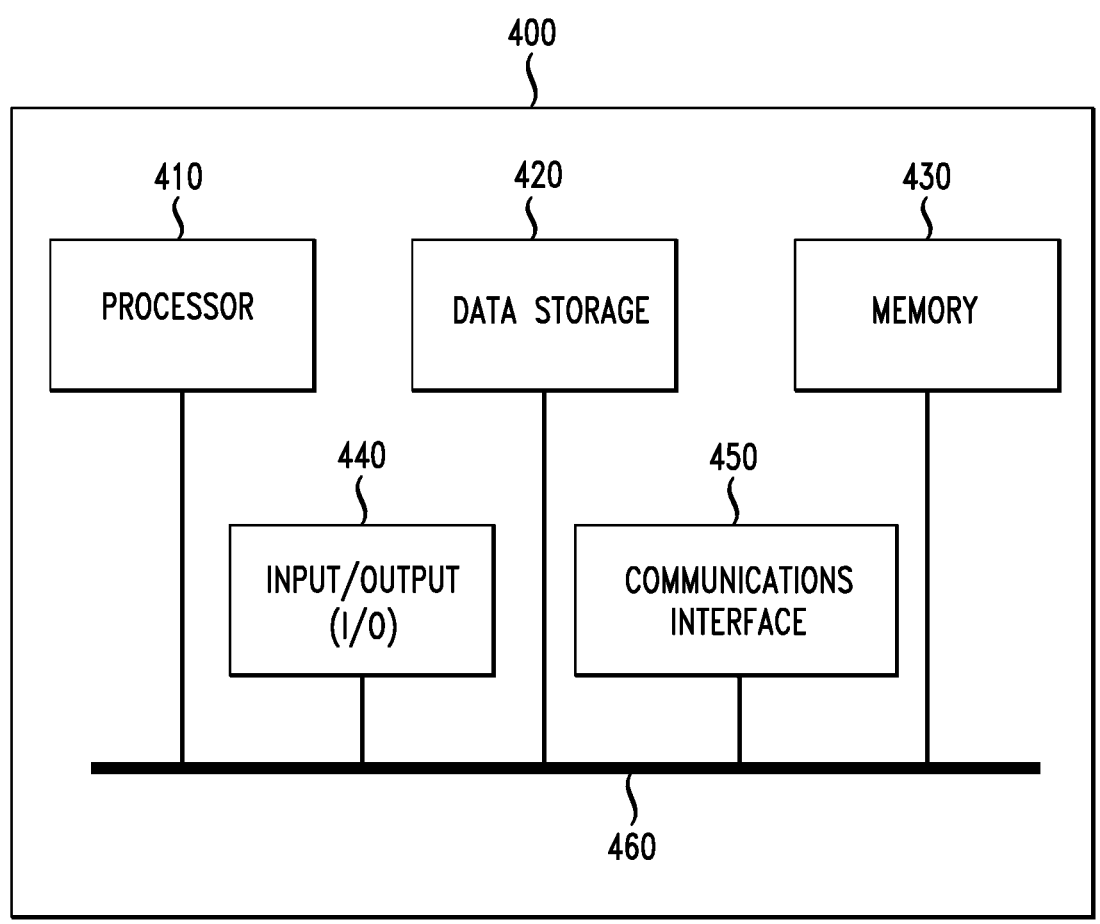
FIG. 4 illustrates a high-level block diagram of an exemplary computer that may be used for implementing multi-clad fiber spot size selection in ophthalmic procedures in accordance with an embodiment.

As detailed above, the various embodiments herein can be embodied in the form of methods and apparatuses for practicing those methods. The disclosed methods may be performed by a combination of hardware, software, firmware, middleware, and computer-readable medium (collectively "computer") installed in and/or communicatively connected to a user device. FIG. 4 is a high-level block diagram of an exemplary computer 400 that may be used for implementing a method for spot size selection for ophthalmic procedures in accordance with the various embodiments herein. Computer 400 comprises a processor 410 operatively coupled to a data storage device 420 and a memory 430. Processor 410 controls the overall operation of computer 400 by executing computer program instructions that define such operations. Communications bus 460 facilitates the coupling and communication between the various components of computer 400. The computer program instructions may be stored in data storage device 420, or a non-transitory computer readable medium, and loaded into memory 430 when execution of the computer program instructions is desired. Thus, the steps of the disclosed method (see, FIG. 3) and the associated discussion herein above) can be defined by the computer program instructions stored in memory 430 and/or data storage device 420 and controlled by processor 410 executing the computer program instructions. For example, the computer program instructions can be implemented as computer executable code programmed by one skilled in the art to perform the illustrative operations defined by the disclosed method. Accordingly, by executing the computer program instructions, processor 410 executes an algorithm defined by the disclosed method. Computer 400 also includes one or more communication interfaces 450 for communicating with other devices via a network (e.g., a wireless communications network) or communications protocol (e.g., Bluetooth®). For example, such communication interfaces may be a receiver, transceiver or modem for exchanging wired or wireless communications in any number of well-known fashions. Computer 400 also includes one or more input/output devices 440 that enable user interaction with computer 400 (e.g., camera, display, keyboard, mouse, speakers, microphone, buttons, etc.).

Processor 410 may include both general and special purpose microprocessors, and may be the sole processor or one of multiple processors of computer 400. Processor 410 may comprise one or more central processing units (CPUs), for example. Processor 410, data storage device 420, and/or memory 430 may include, be supplemented by, or incorporated in, one or more application-specific integrated circuits (ASICs) and/or one or more field programmable gate arrays (FPGAs).

Data storage device 420 and memory 430 each comprise a tangible non-transitory computer readable storage medium. Data storage device 420, and memory 430, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 440 may include peripherals, such as a camera, printer, scanner, display screen, etc. For example, input/output devices 440 may include a display device such as a cathode ray tube (CRT), plasma or liquid crystal display (LCD) monitor for displaying information to the user, a keyboard, and a pointing device such as a mouse or a trackball by which the user can provide input to computer 400.

It should be noted that for clarity of explanation, the illustrative embodiments described herein may be presented as comprising individual functional blocks or combinations of functional blocks. The functions these blocks represent may be provided through the use of either dedicated or shared hardware, including, but not limited to, hardware capable of executing software. Illustrative embodiments may comprise digital signal processor ("DSP") hardware and/or software performing the operation described herein. Thus, for example, it will be appreciated by those skilled in the art that the block diagrams herein represent conceptual views of illustrative functions, operations and/or circuitry of the principles described in the various embodiments herein. Similarly, it will be appreciated that any flowcharts, flow diagrams, state transition diagrams, pseudo code, program code and the like represent various processes which may be substantially represented in computer readable medium and so executed by a computer, machine or processor, whether or not such computer, machine or processor is explicitly shown. One skilled in the art will recognize that an implementation of an actual computer or computer system may have other structures and may contain other components as well, and that a high level representation of some of the components of such a computer is for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for spot size selection, the method comprising:
   receiving, at an optical system, a spot size selection;
   generating a spot size corresponding to the spot size selection by propagating an optical signal using a first cladding of a dual-clad optical fiber;
   receiving, at the optical system, a second spot size selection; and
   generating a second spot size corresponding to the second spot size selection, by propagating the optical signal using a second cladding of the dual-clad optical fiber.

2. The method of claim 1, wherein the propagating the optical signal using the first cladding of the dual-clad optical fiber comprises:
   propagating the optical signal using an inner cladding of the dual-clad optical fiber.

3. The method of claim 1, wherein the propagating the optical signal using the first cladding of the dual-clad optical fiber comprises:
   propagating the optical signal using an outer cladding of the dual-clad optical fiber.

4. The method of claim 1, wherein propagating the optical signal using the first cladding of the dual-clad optical fiber comprises:
   propagating the optical signal through at least one of a plurality of lens arrays.

5. The method of claim 1, wherein the generating the spot size is in response to the receiving, at an optical system, the spot size selection.

6. A method for spot size selection, the method comprising:
   receiving, at an optical system, a spot size selection;
   selecting a dual-clad optical fiber based on the spot size selection, the dual-clad optical fiber comprising an inner cladding and an outer cladding; and
   generating a spot size corresponding to the spot size selection by propagating an optical signal using a cladding of the selected dual-clad optical fiber;
   receiving, at the optical system, a second spot size selection; and
   generating a second spot size corresponding to the second spot size selection, by propagating the optical signal using an other cladding of the dual-clad optical fiber.

7. The method of claim 6, wherein the propagating the optical signal using the cladding of the selected dual clad optical fiber comprises:
   propagating the optical signal using the inner cladding of the selected dual-clad optical fiber.

8. The method of claim 6, wherein the propagating the optical signal using the cladding of the selected dual-clad optical fiber comprises:
    propagating the optical signal using the outer cladding of the selected dual-clad optical fiber.

9. The method of claim 6, wherein propagating the optical signal using the cladding of the selected dual-clad fiber comprises:
    propagating the optical signal through at least one of a plurality of lens arrays.

\* \* \* \* \*

UNITED STATES PATENT AND TRADEMARK OFFICE
CERTIFICATE OF CORRECTION

| | | |
|---|---|---|
| PATENT NO. | : 10,758,415 B2 | |
| APPLICATION NO. | : 15/873129 | |
| DATED | : September 1, 2020 | |
| INVENTOR(S) | : Sramek | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

Signed and Sealed this
Thirty-first Day of January, 2023

*Katherine Kelly Vidal*

Katherine Kelly Vidal
*Director of the United States Patent and Trademark Office*